United States Patent [19]
Pintucci

[11] Patent Number: 5,527,328
[45] Date of Patent: Jun. 18, 1996

[54] APPARATUS TO AUTOMATICALLY POSITION AND OPERATE SURGICAL INSTRUMENTS

[76] Inventor: Stefano Pintucci, No. 37, Via Bertoloni, Rome, Italy, 00197

[21] Appl. No.: 240,701
[22] PCT Filed: Nov. 21, 1991
[86] PCT No.: PCT/IT91/00099
    § 371 Date: May 9, 1994
    § 102(e) Date: May 9, 1994
[87] PCT Pub. No.: WO93/09738
    PCT Pub. Date: May 27, 1993

[30]     Foreign Application Priority Data

Jul. 26, 1990 [IT] Italy ........................... 48173/90

[51] Int. Cl.⁶ ........................................... A61B 17/32
[52] U.S. Cl. ..................... 606/166; 606/1; 606/161; 606/130
[58] Field of Search ................... 606/166, 161, 606/130, 1, 162

[56]         References Cited

U.S. PATENT DOCUMENTS

| | | | |
|---|---|---|---|
| 2,249,906 | 7/1941 | Longoria | 606/166 |
| 2,480,737 | 8/1949 | Jayle . | |
| 4,173,980 | 11/1979 | Curtin . | |
| 4,662,370 | 5/1987 | Hoffmann et al. . | |
| 4,674,503 | 6/1987 | Peyman et al. | 606/166 |
| 4,744,362 | 5/1988 | Gründler . | |
| 4,943,296 | 7/1990 | Funakubo et al. . | |
| 5,133,726 | 7/1992 | Ruiz et al. . | |

FOREIGN PATENT DOCUMENTS

| | | |
|---|---|---|
| 0208950 | 1/1987 | European Pat. Off. . |
| 0239409 | 9/1987 | European Pat. Off. . |
| 0442156 | 8/1991 | European Pat. Off. . |
| 3433581 | 3/1986 | Germany . |
| 3522999 | 1/1987 | Germany .................. 606/166 |

*Primary Examiner*—Stephen C. Pellegrino
*Assistant Examiner*—Michael Peffley
*Attorney, Agent, or Firm*—Beveridge, DeGrandi, Weilacher & Young

[57]         ABSTRACT

An apparatus to automatically position and operate surgical instruments, particularly for refractive keratic surgery, particularly lamellar refractive surgery, which includes a device for correctly positioning the apparatus in correspondence with an operating cot; a device for vertically raising all the apparatus; a horizontal guide, a first support member slideably arranged on the horizontal guide, a horizontal linear actuator, which determines the slide in both directions of the support member on the horizontal guide; a vertical guide, integral with the first support member, and at right angles to the horizontal guide; a second support member slideable in both directions on the vertical guide by way of a first vertical linear actuator; a member for operating and supporting the surgical instrument, borne by the second support member; a horizontal plate integral with the support member and endowed with a second vertical linear actuator which allows its raising and lowering in an autonomous manner, and an arm integral with the device for positioning and the vertical raising and bearing, at its free end, a member for correctly positioning the portion which it is operated upon.

26 Claims, 1 Drawing Sheet

APPARATUS TO AUTOMATICALLY POSITION AND OPERATE SURGICAL INSTRUMENTS

FIELD OF THE INVENTION

The present invention relates to an apparatus to automatically position and operate surgical instruments, in particular for refractive keratic surgery, in particular lamellar refractive surgery.

More particularly, the invention relates to an apparatus of the said type, that allows surgical techniques to be carried out with extreme safety and high repeatability.

BACKGROUND OF THE INVENTION

It is well-known that in all the fields of surgery one tries to realize equipment that allows one to operate to a greater precision, and, moreover, allows surgeons without a great deal of experience to carry out delicate operative surgeries.

This is even more true in those fields wherein delicate organs are operated upon, and therefore there is particularly felt a need for such a device in ophthalmological surgery.

In this field, a very important operation consists in lamellar refractive surgery (keratomyleusis).

Keratomyleusis is a surgical methodology well known to those skilled in the art, originally set forth by Prof. Barraquer.

It has developed during years through three techniques, and the relevant apparatuses have been realized by Barraquer himself, by Krumeich and Swinger and then by Ruiz.

Among the various equipment that makes up the set of the surgical instruments necessary to operate, Barraquer's technique provides the use of a sucking metal ring which is applied on the eye of the patient and whereon the microkeratome slides.

In order to be able to achieve the exact keratic surface protrusion it is necessary to have a complete set of sucking metal rings at one's disposal.

Before carrying out the operation, one measures the intraocular pressure caused by the ring and measures, by means of a precalibrated lens, the lenticule diameter that would be obtained with that particular ring.

Only after verifying these variables and selecting the proper ring, will one be able to proceed to sectioning of the lamella.

Obviously, all these operations render the operation more difficult, less safe and longer.

In the techinque described by Krumeich and Swinger the same type of sucking rings is employed.

In Ruiz's technique, on the contrary, a series of pneumatic rings is employed which present the same already mentioned problems.

Recently, in the Application for Italian Patent No. 48104-A/89 filed on Jun. 21, 1989, an apparatus set has been suggested for carrying out myopical or hypermetropical keratomyleusis wherein a single sucking ring endowed with an adjustment ferrule is provided, for determining the diameter of the flap to be removed, and constituting a track for the sliding of the microkeratome and the precalibrated lens.

As is apparent, such a solution constitutes a considerable progress in comparison with the preceding apparatuses in that it allows one to rapidly determine the diameter of the flap to be removed, to measure intraocular pressure and to carry out the refractive section.

Subsequently, it has been suggested, by the same Applicant, a further improvement of the latter apparatus, and particularly a sucking ring realized with extremely simple mechanics, with a handle that allows a very safe positioning of the ring on the eye of the patient is able to effect decisively considerable excursions both downward and upward.

All that has been disclosed above has allowed the operation technique to be more and more improved. However, each of the improvement techniques described above maintains a very strict link between the result of the operation and the ability of the surgeon.

This is true in that the result is strictly connected with the ability of the surgeon.

Moreover, with these apparatuses of the manual type, it turns out to be very difficult to have a high repeatability of the operation.

SUMMARY OF THE INVENTION

In view of the above, the Applicant has developed an apparatus that allows the aforementioned operative technique to be executed in an automatic and absolutely repeatable manner.

It is therefore the specific object of the present invention to provide an apparatus for automatically positioning and operating surgical instruments, particularly for refractive keratic surgery, particularly lamellar refractive surgery, comprising means for the correct positioning in correspondence with the operating cot; means for vertically raising the entire apparatus; a horizontal guide; a first support member arranged slideably upon said horizontal guide; a horizontal linear actuator, which determines the slide, in both directions, of said support member on the horizontal guide; a vertical guide, integral with said first support member, at right angles to the horizontal guide; a second support member, slideable in both directions upon said vertical guide by means of a first vertical linear actuator; a member for operating and supporting the surgical instrument, borne, by the second support member; a horizontal plane integral with said second support member and endowed with a second vertical linear actuator that allows the raising and the lowering thereof in an autonomous manner; and an arm, integral with said means for positioning and vertically raising and bearing, at its free end, a member for the correct positioning of the portion which is to be operated.

According to the invention, all the operation and the various functions of the apparatus can be controlled through a pre-programmed and surgeon settable central unit.

Preferably, said horizontal linear actuator will be comprised of a continuous current motor, while the two vertical linear actuators will be comprised of two stepper motors.

In a preferred embodiment of the apparatus according to the invention, the member for operating and supporting the surgical instrument can be comprised of a continuous current motor with a spindle bearing, and said surgical instrument is supported thereby either fixedly or removably.

The surgical instrument will be preferably comprised of a rotating blade, case in which the motor and the spindle are preferably arranged at right angles to the vertical guide.

Moreover, a miller for correcting the section can be mounted on said spindle.

Again on the spindle a little spoon for taking in the cut lamella can be provided.

Preferably, said arm, coupled in a fixed or removable manner with said positioning and raising means will bear, at its free end, the sucking ring, connected with the vacuum source, for the positioning of the cornea.

However, according to the type of operation and of the stage of the same, upon the arm a bench for working the lamella can be provided.

The means for the positioning the apparatus of the invention upon the cot can be made up of a magnetic system, brackets or other similar mechanisms.

The means for the vertical raising can be of a mechanical and/or pneumatic and/or hydraulic type.

BRIEF DESCRIPTION OF THE INVENTION

The present invention will be now disclosed, as a matter of illustration, but not of restriction, according to a preferred embodiment thereof represented in the FIGURE of the annexed drawing wherein a schematic side view is shown of the apparatus according to the invention.

DETAILED DESCRIPTION

Figure 1:
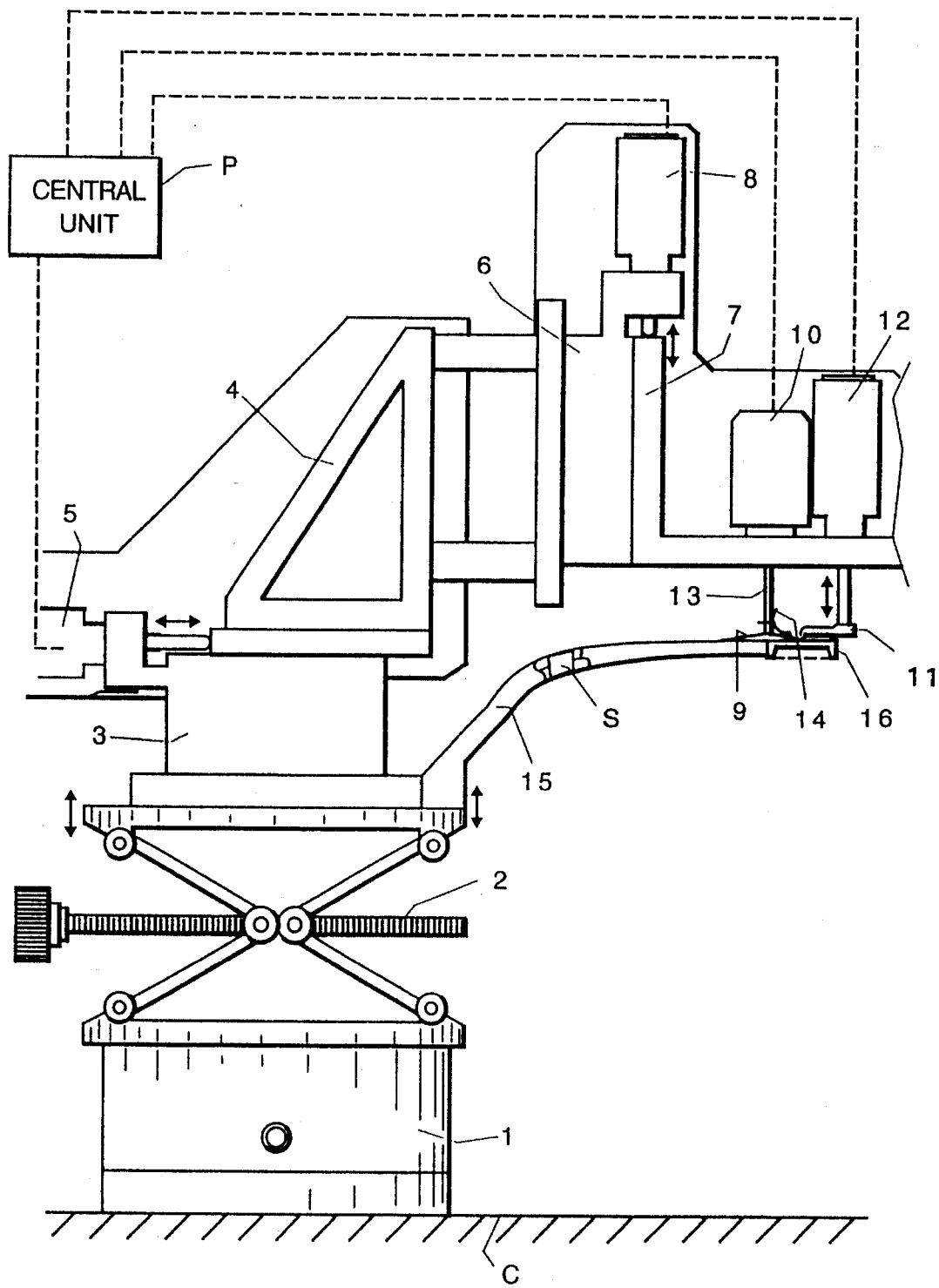

The apparatus shown in the FIGURE provides a connector 1 of a magnetic type for fastening the apparatus to the operative cot C, above which a raising member is provided for raising or lowering all the apparatus above connector 1, so as to be able to correctly position the portion of the apparatus.

A horizontal guide 3 which serves to position, in a known manner, the whole proper surgical instrument with respect to the eye of a patient is supported by connector 1 and raising member 2.

It bears, slideably, a support structure 4 wherewith the rest of the apparatus according to the invention is coupled in an integral manner, in the way that will be seen below.

Said support 4 is made to slide upon the guide 3 by the linear actuator 5, which preferably will be a continuous current (c.c.) motor, in that the type of action that it has to perform requires a continuous linear movement.

At the extremity, opposite that for the coupling with the guide 3, the support 4 integrally bears a vertical guide 6 at right angles to the guide 3.

Upon said vertical guide 6, a second support 7 slides when actuated by the linear actuator 8 which, in this case, is preferably a stepper motor.

Said support 7 has a vertical arm, which slides upon the vertical guide 6 and a horizontal arm which bears the blade for cutting 9, and the relevant c.c. motor 10, and the plane 11 with the relevant vertical linear actuator 12.

On the arm 13 of the blade 9 a little spoon 14 for picking the cut lamella is provided.

Obviously, to the arm 13 a tool different from the blade 9 can be applied, e.g. a miller, to carry out further stages of the operative surgery.

To said member 2 an arm 15 is coupled in an integral, but removable manner, such that at its extremity the free end of the arm is positioned under the blade 9 and the plane 11. The arm 15 includes sucking ring 16.

The sucking system S of the sucking ring 16 can be provided inside the arm 15.

As will be seen in the following, the plane 11 allows the cut thickness to be adjusted, while the raising and lowering of blade 9 through movement of arm 13, which rises and drops integrally with the support 7, provides for diameter adjustments.

In the place of the arm 15 and of the ring 16 other members necessary to carry out subsequent stages of the operative surgery can be provided.

All the operation of the various actuators 5, 8, 10 and 12 can be controlled by a pre-programmed central unit instructable step by step during the operative surgery.

Compared with the sucking ring employed for the manual execution of keratomyleusis operation, the ring 16 need not be endowed with the prior art guides for the slide of the microkeratome, the handle and the raising and lowering mechanisms for finding the zero and determining the thickness of the cut or section.

To initiate an operative surgery with the apparatus represented in the FIGURE, it is first of all necessary to proceed to set all the instruments to zero.

This is achieved by bringing, by means of the horizontal actuator 5 and the vertical actuator 8, the blade 9 into contact with the ring 16, after completely raising the plane 11.

The ring 16 will be electrically insulated with respect to the other components.

When the blade 9 and the ring 16 are in contact one is in the ideal position for the maximum diameter and maximum thickness section. This is the first reference point.

The actuator 12 also is insulated with respect to the actuator 10.

Then one lowers the plane 11 so as to touch the sucking ring 16, i.e. in a potential condition of zero thickness section. This is the second reference point.

Then one reraises the whole by a known quantity, by means of the actuator 8.

At this point it is necessary to bring the eye of the patient in correspondence with the sucking ring 16.

The patient is layed down and is made to stare at a luminous point, marking the centre of the cornea.

After the anaesthesia and applying the usual operative techniques, one positions the apparatus on the operative cot, causing the sucking ring 16 to find itself above the eye of the patient.

Before applying the vacuum on the ring, one brings, through the actuator 5, all the instrument in a withdrawn position, and makes the patient stare upward in such a manner as to make the center of the sucking ring correspond with the center of the cornea.

Then one applies the vacuum and the eye is fixed in position.

The member 2 is no more touched. The system is stationary.

Then one measures the pressure of the eye and the proper operation can be initiated.

Through the actuator 5 the blade 9 and the plane 11 are brought onto the ring 16 and then, through the vertical actuator 8 one lowers the blade 9, kept firm, up to skim the eye of the patient.

The cornea of the patient being a conductor, when the blade 9 skims it, one has another reference point of the system.

Indeed, from this point, the more the blade 9 is lowered, the greater the diameter of the section.

One withdraws the blade 9 backwards, horizontally, through the actuator 5 and lowers it by the quantity necessary to achieve the section of the desired diameter.

In this position, the plane 11 will go to find itself on the eye of the patient and thus can be considered a contact member with respect to the eye.

By acting now on the vertical actuator 12, by raising the plane 11, one determines the desired thickness of the section.

At this point, one actuates the motor 10, making the blade 9 to rotate and the horizontal actuator 5 to push support structure 4 and the components represented by reference numbers 6, 7, 8, 9, 10, 11 and 12 supported thereby, achieving the section.

After finishing the section, one raises the components supported by raising member 2 and brings support structure 4 and supported components 6–12 back.

To operate according to Ruiz's technique, it will suffice to execute the second section and then reapply the first removed lamella.

Where, on the contrary, it is desired to execute Krumeich's technique, it will suffice to remove the arm 15 with the sucking ring 16 and substitute it with a bench assembly B for working the lamella.

One executes the correction of the lamella which will thereafter be reapplied to the patient.

The blade 9, moreover, can be substituted by a miller for correcting the section where the existence of a step on the section is recognized.

The present invention has been described with specific reference to some of the preferred embodiments, but it is to be understood that variations and/or modifications can be made by those skilled in the art, without so getting out of the relevant protection scope.

I claim:

1. An apparatus for surgery, comprising:
    a base support member for contact with an underlying support surface,
    a raising member for lifting a surgical assembly vertically with respect to said base support member, said raising member being supported by said base support member, and said surgical assembly comprising,
    (a) a horizontal guide supported by said raising member,
    (b) a first support member adjustably supported by said horizontal guide,
    (c) a horizontal linear actuator in contact with said first support member for controlling an adjustment length of said first support member with respect to said horizontal guide,
    (d) a vertical guide joined with said first support member,
    (e) a second support member in engagement with said vertical guide so as to be adjustable both in an up and a down vertical direction along a vertical axis, and said second support member including a platform,
    (f) a first vertical linear actuator in contact with said second support member for adjusting said second support member and platform in both an up and a down vertical direction along the vertical axis,
    (g) a member for operating and supporting a surgical instrument, said member for operating and supporting a surgical instrument being supported by said platform,
    (h) a contact member dimensioned for contact with an anatomical portion to be operated upon,
    (i) a second vertical actuator supported by said platform and being independently vertically adjustable with respect to said platform, said contact member being joined with said second vertical actuator such that said contact member is vertically adjustable in an autonomous manner with respect to said platform,
    (j) an arm having a first end connected to at least one of said raising member and said horizontal guide, and said arm having a free end extending below said member for operating and supporting a surgical instrument and said free end bearing a positioning member for positioning an anatomical portion to be operated upon.

2. The apparatus according to claim 1, further comprising a pre-programmed surgeon setable central unit in communication with and automatically controlling said horizontal linear actuator, said first and second vertical linear actuators, and said member for operating and supporting the surgical instrument.

3. The apparatus according to claim 1, characterized in that said horizontal linear actuator is comprised of a continuous current motor.

4. The apparatus according to one of claim 1, characterized in that said first vertical linear actuator is made up of a stepper motor.

5. The apparatus according to one of claim 4, characterized in that said second vertical linear actuator is made up of a stepper motor.

6. The apparatus according to claim 1 further comprising a surgical instrument and said member for operating and supporting a surgical instrument is comprised of a driving motor and of a spindle, with said spindle bearing, at a free end thereof, said surgical instrument.

7. The apparatus according to claim 6, characterized in that said surgical instrument is comprised of a rotating blade.

8. The apparatus according to claim 6, characterized in that said surgical instrument is comprised of an oscillating blade.

9. The apparatus according to claim 6, characterized in that said surgical instrument mounted on said spindle is a miller.

10. The apparatus according to claim 6 wherein a spoon member for taking in a cut lamella is provided on said spindle.

11. The apparatus according to claim 1 further comprising a suction system and said positioning member including a sucking ring which is connected with said suction system.

12. The apparatus according to claim 1 characterized in that said base support member includes a magnetic connector for connecting said base support member to the underlying support surface.

13. An apparatus as recited in claim 1 wherein said positioning member is an optical fixation device for fixing an eye of a patient in position, and said apparatus further comprising a surgical instrument which includes a blade and which is supported by said member for operating and supporting a surgical instrument and said contact member includes a planar eye contact surface.

14. An apparatus as recited in claim 13 wherein said member for operating and supporting a surgical instrument includes means for rotating said blade, and said optical fixation device includes a suction ring.

15. An apparatus as recited in claim 1 further comprising a surgical instrument fixed to said member for operating and supporting a surgical instrument, said surgical instrument being a blade, and said member for operating and supporting a surgical instrument including a driving motor and a spindle wherein said blade is supported by said spindle and rotated by said spindle upon operation of said driving motor.

16. An apparatus as recited in claim 1 wherein said support base includes connection means for securing said support base into a fixed position with respect to an underlying support surface.

17. An apparatus as recited in claim 16 wherein said connection means includes a magnetic device for securing said support base to a metallic underlying surface.

18. An ophthalmological apparatus for eye surgery, comprising:

a base support member for contact with an underlying support surface, a raising member for lifting a surgical assembly vertically with respect to said base support member, said raising member being supported by said base support member, and said surgical assembly comprising, (a) a horizontal guide supported by said raising member, (b) a first support member arranged, slideably, on said horizontal guide, (c) a horizontal linear actuator in contact with said first support member for controlling a sliding length of said first support member with respect to said horizontal guide, (d) a vertical guide supported by said first support member, (e) a second support member in sliding engagement with said vertical guide so as to be slideable both in an up and a down direction along a vertical axis, and said second support member including a platform, (f) a first vertical linear actuator in contact with said second support member for adjusting said second support member and platform in both directions along the vertical axis, (g) a member for operating and supporting a surgical instrument, said member for operating and supporting a surgical instrument being supported by said platform, (h) a planar contact member dimensioned for contact with the eye, (i) a second vertical actuator supported by said platform and independently vertically adjustable with respect to said platform, and said contact member being joined with said second vertical actuator such that said contact member is vertically adjustable in an autonomous manner with respect to said platform, (j) an arm having a first end connected to at least one of said raising member and said horizontal guide, and said arm having a free end extending below said member for operating and supporting a surgical instrument and said free end bearing an ocular fixation unit for engagement with and fixation of an eyeball to be operated upon.

19. An apparatus as recited in claim 18 wherein said ocular fixation unit includes a suction ring and a suction system in communication with said suction ring.

20. An apparatus as recited in claim 19 wherein said suction system is positioned, at least in part, within a cavity in said arm.

21. An apparatus as recited in claim 18 further comprising a surgical instrument which forms an integral component of said member for operating and supporting a surgical instrument.

22. An apparatus as recited in claim 18 further comprising a surgical instrument releasably attached to a distal end of said member for operating and supporting a surgical instrument.

23. An apparatus as recited in claim 18 further comprising a surgical instrument that extends off from a support component of said member for operating and supporting a surgical instrument and which surgical instrument is dimensioned for refractive keratic surgery.

24. An apparatus as recited in claim 23 wherein said surgical instrument is a disk blade and said member for operating and supporting a surgical instrument includes means for rotating said blade, and said contact member includes a planar extension member for contact with the eye whereby a cutting of a lamella portion of the eye to a desired thickness is facilitated.

25. An apparatus as recited in claim 24 further comprising a lamella pick up spoon attached to said member for operating and supporting a surgical instrument.

26. An apparatus as recited in claim 18 wherein said arm is a curved beam having one end rigidly fixed to said raising member, an intermediate area which curves upwardly away from said raising member, and a free end spaced below said platform.

* * * * *